United States Patent
Yamamoto et al.

(10) Patent No.: US 12,117,784 B2
(45) Date of Patent: Oct. 15, 2024

(54) APPARATUS, METHOD AND STORAGE MEDIUM

(71) Applicant: YOKOGAWA ELECTRIC CORPORATION, Tokyo (JP)

(72) Inventors: Junji Yamamoto, Tokyo (JP); Hiroaki Kanokogi, Tokyo (JP); Keiichiro Kobuchi, Tokyo (JP); Yota Furukawa, Tokyo (JP); Rei Karasawa, Tokyo (JP); Hiroto Abe, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 1031 days.

(21) Appl. No.: 17/074,648

(22) Filed: Oct. 20, 2020

(65) Prior Publication Data

US 2021/0132556 A1    May 6, 2021

(30) Foreign Application Priority Data

Oct. 31, 2019  (JP) ................................ 2019-198308

(51) Int. Cl.
*G05B 13/04* (2006.01)
*C12M 1/36* (2006.01)
*G05B 13/02* (2006.01)

(52) U.S. Cl.
CPC .......... *G05B 13/048* (2013.01); *C12M 41/48* (2013.01); *G05B 13/0265* (2013.01)

(58) Field of Classification Search
CPC ..... G05B 15/02; G05B 13/0265; C12M 41/48
(Continued)

(56) References Cited

U.S. PATENT DOCUMENTS

2017/0016354 A1   1/2017  Zhang
2017/0031335 A1*  2/2017  Sakakibara .......... G05B 19/042
(Continued)

FOREIGN PATENT DOCUMENTS

CA   2525594 A1 *  2/2005 .......... G05B 19/418
EP   3428744 A1    1/2019
(Continued)

OTHER PUBLICATIONS

Office Action issued for counterpart Japanese Application No. 2019-198308, issued by the Japan Patent Office on Apr. 26, 2022 (drafted on Apr. 20, 2022).
(Continued)

*Primary Examiner* — Ronald D Hartman, Jr.

(57) ABSTRACT

An apparatus is provided, which includes a setting unit for setting an operation content for a manufacturing system configured to manufacture an object to be manufactured, a first acquisition unit for acquiring a posterior state parameter set indicating a state of at least one of the manufacturing system or the object to be manufactured after the operation content is set, and a learning processing unit for executing, by using learning data including the operation content and the posterior state parameter set, a learning process of a control model of the manufacturing system configured to output the operation content that increases a reward value determined by a preset reward function in response to input of a state parameter set indicating a state of at least one of the manufacturing system or the object to be manufactured.

16 Claims, 8 Drawing Sheets

(58) Field of Classification Search
USPC .......................................................... 700/47
See application file for complete search history.

(56) References Cited

U.S. PATENT DOCUMENTS

| | | | |
|---|---|---|---|
| 2017/0185076 A1* | 6/2017 | Yamamoto | ....... G05B 19/41865 |
| 2018/0373223 A1 | 12/2018 | Ikai | |
| 2019/0265686 A1* | 8/2019 | Obata | ................ G05B 19/4188 |
| 2019/0317472 A1 | 10/2019 | Zhi | |
| 2020/0014761 A1 | 1/2020 | Kawaai | |

FOREIGN PATENT DOCUMENTS

| | | | | |
|---|---|---|---|---|
| JP | 2013041173 A | | 2/2013 | |
| JP | 2019145042 A | * | 8/2019 | ....... G05B 19/41875 |
| WO | 9215964 A1 | | 9/1992 | |
| WO | WO-2005010627 A2 | * | 2/2005 | ....... G05B 19/41875 |
| WO | 2010002745 A1 | | 1/2010 | |
| WO | 2018173121 A1 | | 9/2018 | |
| WO | WO-2018210816 A1 | * | 11/2018 | ....... G05B 19/41865 |
| WO | 2018229802 A1 | | 12/2018 | |
| WO | 2019126535 A1 | | 6/2019 | |

OTHER PUBLICATIONS

European Office Action for European Patent Application No. 20204966.4, issued by the European Patent Office on Jan. 14, 2022.

Kamekura Koichi et al., "Biopharmaceutical Manufacturing Facility," Journal of IHI Technologies, vol. 49(2), 2009, p. 67-p. 73.

Shioya Suteaki, "Optimization of Culture Operations and Realization Thereof," Journal of the Society of Instrument and Control Engineers, vol. 34(1), 1995, p. 11-p. 17.

Omasa Takeshi, "Engineering Science for Production of Biologics,"Journal of bioscience and bioengineering, vol. 91(9), 2013, p. 507-p. 510.

Matsuzaki Junichi, "Current Status and Issues of Biopharmaceutical Industry," Journal of bioscience and bioengineering, vol. 91(9), 2013, p. 495-p. 498.

Extended European Search Report for European Patent Application No. 20204966.4, issued by the European Patent Office on Mar. 15, 2021.

* cited by examiner

| INPUT (STATE PARAMETER SET) | | OUTPUT (OPERATION CONTENT) | |
|---|---|---|---|
| STATE PARAMETER $I_A$ | STATE PARAMETER $I_B$ (KPI) | ACTIVE VARIABLE $O_A$ | ACTIVE VARIABLE $O_B$ |
| $I_{A1}$ | $I_{B1}$ | $O_{A1}, O'_{A1}, O''_{A1}$ | $O_{B1}, O'_{B1}, O''_{B1}$ |
| $I_{A2}$ | $I_{B2}$ | $O_{A2}, O'_{A2}, O''_{A2}$ | $O_{B2}, O'_{B2}, O''_{B2}$ |
| $I_{A3}$ | $I_{B3}$ | $O_{A3}, O'_{A3}, O''_{A3}$ | $O_{B3}, O'_{B3}, O''_{B3}$ |
| $I_{A4}$ | $I_{B4}$ | $O_{A4}, O'_{A4}, O''_{A4}$ | $O_{B4}, O'_{B4}, O''_{B4}$ |
| ... | ... | ... | ... |
| $I_{AN}$ | $I_{BN}$ | $O_{AN}, O'_{AN}, O''_{AN}$ | $O_{BN}, O'_{BN}, O''_{BN}$ |

FIG. 2

| INPUT (STATE PARAMETER SET) | | OUTPUT (OPERATION CONTENT) | |
|---|---|---|---|
| STATE PARAMETER $I_A$ | STATE PARAMETER $I_B$ (KPI) | ACTIVE VARIABLE $O_A$ | ACTIVE VARIABLE $O_B$ |
| $I_{A1}$ | $I_{B1}$ | $O_{A1}$ | $O_{B1}$ |
| $I_{A2}$ | $I_{B2}$ | $O_{A2}$ | $O_{B2}$ |
| $I_{A3}$ | $I_{B3}$ | $O_{A3}$ | $O_{B3}$ |
| $I_{A4}$ | $I_{B4}$ | $O_{A4}$ | $O_{B4}$ |
| ... | ... | ... | ... |
| $I_{AM}$ | $I_{BN}$ | $O_{AM}$ | $O_{BN}$ |

FIG. 3

| PRIOR STATE PARAMETER SET | | OPERATION CONTENT | | POSTERIOR STATE PARAMETER SET | |
|---|---|---|---|---|---|
| STATE PARAMETER $I_A$ | STATE PARAMETER $I_B$ (KPI) | ACTIVE VARIABLE $O_A$ | ACTIVE VARIABLE $O_B$ | STATE PARAMETER $I_{A\_next}$ | STATE PARAMETER $I_{B\_next}$ |
| $I_{A1}$ | $I_{B1}$ | $O_{A1}$ | $O_{B1}$ | $I_{A2}$ | $I_{B2}$ |
| $I_{A2}$ | $I_{B2}$ | $O_{A2}$ | $O_{B2}$ | $I_{A4}$ | $I_{B4}$ |
| $I_{A3}$ | $I_{B3}$ | $O_{A3}$ | $O_{B3}$ | $I_{AN-1}$ | $I_{AN-1}$ |
| $I_{A4}$ | $I_{B4}$ | $O_{A4}$ | $O_{B4}$ | $I_{AN}$ | $I_{BN}$ |
| ... | ... | ... | ... | ... | ... |
| $I_{AN}$ | $I_{BN}$ | $O_{AN}$ | $O_{BN}$ | $I_{A3}$ | $I_{B3}$ |

APPARATUS, METHOD AND STORAGE MEDIUM

The contents of the following Japanese patent application (s) are incorporated herein by reference:
2019-198308 filed in JP on Oct. 31, 2019.

BACKGROUND

1. Technical Field

The present invention relates to an apparatus, a method, and a program.

2. Related Art

Conventionally, in a manufacturing system of a cell or the like, a variety of methods for efficient manufacturing are proposed (for example, see Non-Patent Documents 1 to 4.)
Non-Patent Document 1: Kamekura Koichi et al., "Biopharmaceutical Manufacturing Facility," Journal of IHI Technologies, Vol. 49(2), 2009, p. 67-p. 73.
Non-Patent Document 2: SHIOYA Suteaki, "Optimization of Culture Operations and Realization Thereof," Journal of the Society of Instrument and Control Engineers, Vol. 34(1), 1995, p. 11-p. 17.
Non-Patent Document 3: OMASA Takeshi, "Engineering Science for Production of Biologics," Journal of bioscience and bioengineering, Vol. 91(9), 2013, p. 507-p. 510.
Non-Patent Document 4: MATSUZAKI Junichi, "Current Status and Issues of Biopharmaceutical Industry," Journal of bioscience and bioengineering, Vol. 91(9), 2013, p. 495-p. 498.

However, a suitable operation content for the manufacturing system may not be obtained by the conventional methods.

SUMMARY

In order to solve the above-mentioned problem, a first aspect of the present invention provides an apparatus. The apparatus may include a setting unit for setting an operation content for a manufacturing system configured to manufacture an object to be manufactured. The apparatus may include a first acquisition unit for acquiring a posterior state parameter set indicating a state of at least one of the manufacturing system or the object to be manufactured after the operation content is set. The apparatus may include a learning processing unit for executing, by using learning data including the operation content and the posterior state parameter set, a learning process of a control model of the manufacturing system configured to output the operation content that increases a reward value determined by a preset reward function in response to input of a state parameter set indicating a state of at least one of the manufacturing system or the object to be manufactured.

The learning processing unit may be configured to, in a case where an increase width of the reward value according to a setting result of one said operation content outputted in response to one said state parameter set being input to the control model is less than a reference width, execute the learning process of the control model not to output the one operation content in response to input of the one state parameter set.

The operation content may have a plurality of types of active variables actively settable for the manufacturing system. The learning processing unit may be configured to, in a case where a first operation content and a second operation content in which only values of one active variable of the plurality of types of active variables are different to each other are outputted in response to one said state parameter set being input to the control model, and the difference between reward values according to the result of separately setting each of the first operation content and the second operation content in a state indicated by the one state parameter set is less than a reference width, execute the learning process of the control model to output the operation content that does not include the one active variable of the plurality of types of active variables in response to input of the one state parameter set.

The apparatus may further include a first storage unit for storing a plurality of variation patterns of the operation content. In a case where a plurality of operation contents are acquired in response to input of one said state parameter set to the control model, the setting unit may be configured to set any one of the plurality of operation contents so that each variation pattern in the first storage unit and a variation pattern of the operation content set by the setting unit do not match.

The apparatus may further include a first storage unit for storing a plurality of variation patterns of the operation content. The reward value, in a case where it is set by the setting unit, may be calculated to be lower for the operation content that forms a variation pattern that matches any of the variation patterns in the first storage unit.

The apparatus may further include an environment information acquisition unit for acquiring environment information indicating an external environment of the manufacturing system. The learning processing unit may be configured to execute the learning process of the control model for each external environment.

The learning processing unit may be configured to execute transfer learning for one external environment by using the control model on which the learning process has been executed and execute the learning process for another external environment.

The apparatus may further include a second acquisition unit for acquiring the state parameter set. The apparatus may further include a parameter input unit for inputting the state parameter set acquired by the second acquisition unit to the control model. The apparatus may further include a third acquisition unit for acquiring the operation content outputted from the control model in response to input of the state parameter set to the control model. The setting unit may be configured to set the operation content acquired by the third acquisition unit for the manufacturing system.

The apparatus may further include a calculation unit for calculating the reward value from at least one posterior state parameter included in the posterior state parameter set. The learning processing unit may be configured to execute the learning process by further using the reward value calculated by the calculation unit.

The learning processing unit may be configured to, in a case where the reward value calculated by the calculation unit satisfies a target condition as a result of one said operation content outputted in response to input of one said state parameter set to the control model is set for the manufacturing system and, execute the learning process of the control model so that the one operation content is outputted in response to input of the one state parameter set. The apparatus may further include an output unit for outputting the one operation content and the one state parameter set in association with each other.

The apparatus may further include a control unit for causing manufacturing of the object to be manufactured by causing repeated serial execution of acquisition of the state parameter set by the second acquisition unit, acquisition of the operation content by the third acquisition unit, and setting of the operation content by the setting unit.

The apparatus may further include a second storage unit for accumulating and storing, in a case where one said operation content outputted in response to one said state parameter set being input to the control model is set for the manufacturing system and one said posterior state parameter set is acquired, and in a case where the reward value calculated based on the one posterior state parameter set satisfies a target condition, the one operation content, the one state parameter set, and the one posterior state parameter set in association with each other, The apparatus may further include a prediction unit for predicting, based on a stored content of the second storage unit, a value transition according to at least one posterior state parameter included in each posterior state parameter set when successively setting operation contents in which the reward value satisfies the target condition from a state indicated by the state parameter set acquired by the second acquisition unit.

The posterior state parameter set may include an amount of a foreign body that exists in at least one of the manufacturing system or the object to be manufactured. In a case where the amount of the foreign body is predicted to exceed an upper limit value, the prediction unit may be configured to inform to that effect.

The apparatus may further include a third storage unit for accumulating and storing the learning data. The apparatus may further include a detection unit for detecting, among a plurality of the posterior state parameter sets in the third storage unit, at least one of a common content between the operation contents corresponding to two or more of the posterior state parameter sets that do not satisfy a reference condition or a common content between the operation contents corresponding to two or more of the posterior state parameter sets that satisfy the reference condition.

A second aspect of the present invention provides an apparatus. The apparatus may include a second acquisition unit for acquiring a state parameter set indicating a state of at least one of a manufacturing system or an object to be manufactured by the manufacturing system. The apparatus may include a parameter input unit for inputting the state parameter set acquired by the second acquisition unit to a control model of the manufacturing system configured to output an operation content that increases a reward value determined by a preset reward function in response to input of the state parameter set. The apparatus may include a third acquisition unit for acquiring the operation content outputted from the control model in response to input of the state parameter set to the control model.

The manufacturing system may be a system configured to culture a cell.

A third aspect of the present invention provides a method. The method may include setting an operation content for a manufacturing system configured to manufacture an object to be manufactured. The method may include firstly acquiring a posterior state parameter set indicating a state of at least one of the manufacturing system or the object to be manufactured after the operation content is set. The method may include executing, by using learning data including the operation content and the posterior state parameter set, a learning process of a control model of the manufacturing system configured to output the operation content that increases a reward value determined by a preset reward function in response to input of a state parameter set indicating a state of at least one of the manufacturing system or the object to be manufactured.

A fourth aspect of the present invention provides a method. The method may include secondly acquiring a state parameter set indicating a state of at least one of a manufacturing system or an object to be manufactured by the manufacturing system. The method may include inputting the state parameter set acquired by the secondly acquiring to a control model of the manufacturing system configured to output an operation content that increases a reward value determined by a preset reward function in response to input of the state parameter set. The method may include thirdly acquiring the operation content outputted from the control model in response to input of the state parameter set to the control model.

A fifth aspect of the present invention provides a storage medium having recorded thereon a program. The program may cause a computer to function as a setting unit for setting an operation content for a manufacturing system configured to manufacture an object to be manufactured. The program may cause the computer to function as a first acquisition unit for acquiring a posterior state parameter set indicating a state of at least one of the manufacturing system or the object to be manufactured after the operation content is set. The program may cause the computer to function as a learning processing unit for executing, by using learning data including the operation content and the posterior state parameter set, a learning process of a control model of the manufacturing system configured to output the operation content that increases a reward value determined by a preset reward function in response to input of a state parameter set indicating a state of at least one of the manufacturing system or the object to be manufactured.

A sixth aspect of the present invention provides a storage medium having recorded thereon a program. The program may cause a computer to function as a second acquisition unit for acquiring a state parameter set indicating a state of at least one of a manufacturing system or an object to be manufactured by the manufacturing system. The program may cause the computer to function as a parameter input unit for inputting the state parameter set acquired by the second acquisition unit to a control model of the manufacturing system configured to output an operation content that increases a reward value determined by a preset reward function in response to input of the state parameter set. The program may cause the computer to function as a third acquisition unit for acquiring the operation content outputted from the control model in response to input of the state parameter set to the control model.

The summary clause does not necessarily describe all necessary features of the embodiments of the present invention. The present invention may also be a sub-combination of the features described above.

BRIEF DESCRIPTION OF THE DRAWINGS

FIG. 2 shows the input/output of a control model 312 at an initial stage of learning.

FIG. 3 shows the input/output of the control model 312 after completion of learning.

FIG. 4 shows a stored content of a second storage unit 322.

DESCRIPTION OF EXEMPLARY EMBODIMENTS

Hereinafter, the present invention is described through the embodiments of the invention. However, the embodiments described below do not limit the invention defined in the claims. In addition, not all combinations of features described in the embodiments are necessarily essential to solving means of the invention.

1. System 1

Figure 1:
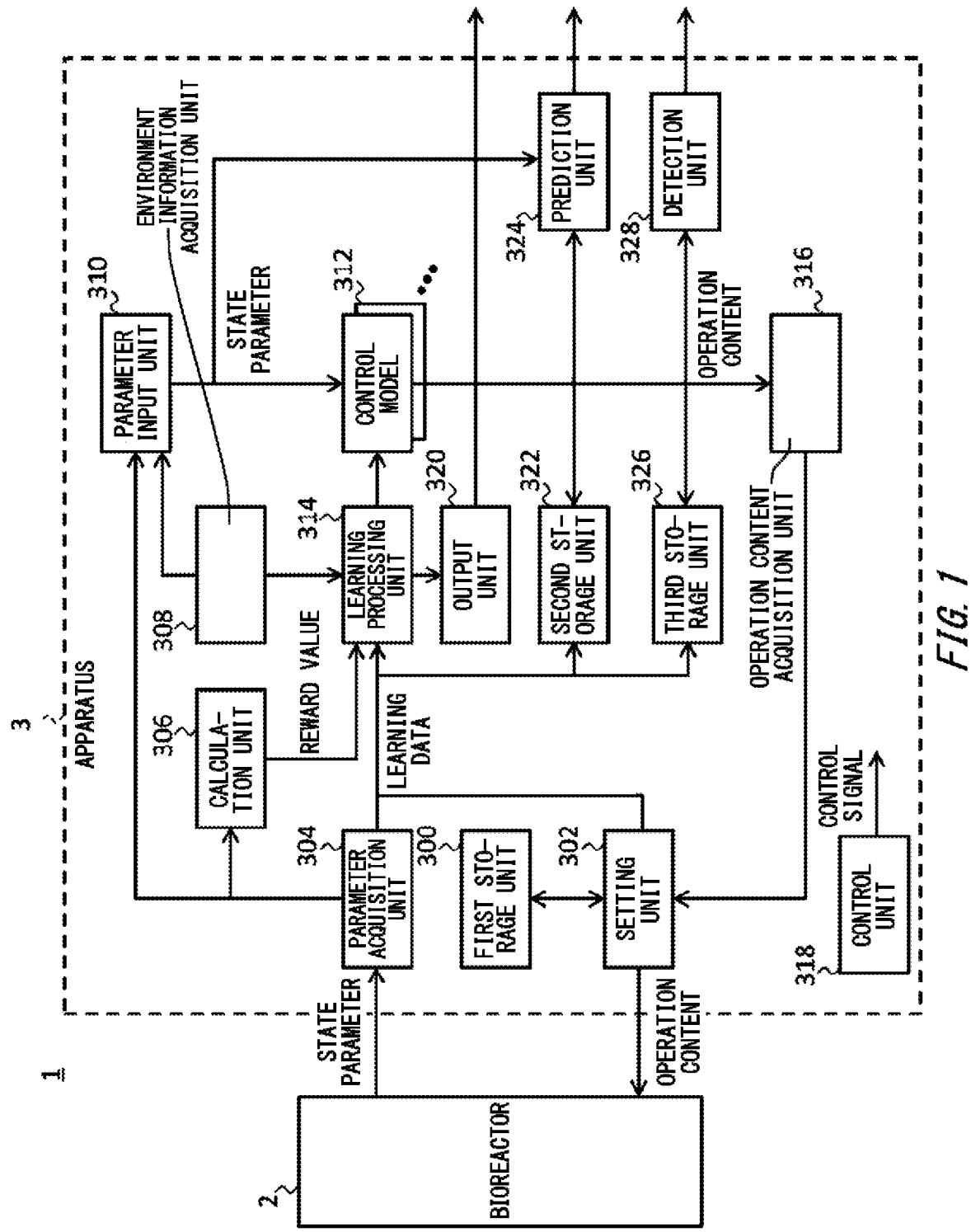
FIG. 1 shows a system 1 according to the present embodiment.

FIG. 1 shows a system 1 according to the present embodiment. The system 1 includes a bioreactor 2 and an apparatus 3.

[1.1. Bioreactor 2] The bioreactor 2 is one example of a manufacturing system configured to manufacture an object to be manufactured. The bioreactor 2 may culture a cell having a particular function (as one example, a function of generating a particular protein) and manufacture the cell as the object to be manufactured. The bioreactor 2 is configured to operate according to an operation content inputted from the outside and change a state of the bioreactor 2 and hence a state of the cell.

The operation content indicates a content of an operation performed in the bioreactor 2 and, in the present embodiment, as one example, indicates an operation content continuously performed within a reference time period. The operation content may have at least one type (in the present embodiment, a plurality of types) of active variables actively settable for the bioreactor 2. Active variables included in each operation content may be of the same type or at least some of the active variables may be of different types. The active variables may include at least one of a set point (target value) of a process value, a manipulate variable, an equipment requirement for manufacturing, or a processing order (procedure.)

The set point of the process value may be, as one example, a temperature set point, a pH set point, or the like. The manipulate variable may be, as one example, power supplied to a heater, an input amount of medium, an input amount of an acid and alkaline solution, a rotation speed of agitation wings for agitating broth or internal gas, a ventilation amount of a reaction tank, or the like. The equipment requirement may be, as one example, a structure or material of the reaction tank, a shape of agitation wings for agitating the broth, a ventilation method of the reaction tank, or the like.

The state of the bioreactor 2 may be, as one example, a temperature of the broth, a pH, a flow speed of the broth, an oxygen concentration, a carbon dioxide concentration and a concentration of nutrients in the broth, an amount of a foreign body that exists in the bioreactor 2, a pressure of the reaction tank, or the like. The state of the cell may be an yield, homogeneity, functionality (as one example, an ability to generate a particular protein), a concentration, the number, distribution, size, weight, production amount (increased amount) of the cell to be cultured, shear stress applied to the cell due to agitation of the broth or the like, an amount of a foreign body that exists in the cell, or the like. The amount of the foreign body may be an absolute amount or a relative amount (as one example, a ratio) to the total amount.

[1.2. Apparatus 3]

The apparatus 3 is configured to assist cell culture in the bioreactor 2. The apparatus 3 includes a first storage unit 300, a setting unit 302, a parameter acquisition unit 304, a calculation unit 306, an environment information acquisition unit 308, a parameter input unit 310, one or plurality of control models 312, a learning processing unit 314, an operation content acquisition unit 316, a control unit 318, an output unit 320, a second storage unit 322, a prediction unit 324, a third storage unit 326, and a detection unit 328.

[1.2.1. First storage unit 300]

The first storage unit 300 is configured to store a plurality of variation patterns of an operation content. The variation patterns to be stored may be known variation patterns, as one example.

[1.2.2. Setting unit 302]

The setting unit 302 is configured to set an operation content for the bioreactor 2. The setting unit 302 may set an operation content for each reference time period. The setting unit 302 may set an operation content provided from the operation content acquisition unit 316 for the bioreactor 2. When a plurality of operation contents are provided for one reference time period from the operation content acquisition unit 316, as detailed below, the setting unit 302 may select one operation content based on the variation patterns in the first storage unit 300 and set the one operation content for the bioreactor 2. The setting unit 302 may provide the set operation content to the learning processing unit 314, the second storage unit 322 and the third storage unit 326.

[1.2.3. Parameter acquisition unit 304]

The parameter acquisition unit 304 is one example of a first acquisition unit and a second acquisition unit, and is configured to acquire a state parameter set indicating a state of at least one of the bioreactor 2 or the cell. The state parameter set may indicate the state at the time of acquisition (as one example, at the present time.) The state parameter set may be referred to as a posterior state parameter set when acquired at a time point after the operation content is set by the setting unit 302 or a prior state parameter set when acquired at a time point before the operation content is set by the setting unit 302. The state parameter set may include at least one state parameter indicating a state of at least one of the bioreactor 2 or the cell.

The parameter acquisition unit 304 may acquire a state parameter set by observing the bioreactor 2, may acquire a state parameter set from a sensor (not shown) provided in the bioreactor 2, may acquire a state parameter set from an operator who has checked the bioreactor 2 or the sensor, or may acquire a state parameter set by integrating a plurality of state parameters acquired by the combination of the above. The state parameter acquired from the operator may be a numerical range. Moreover, the state parameter acquired from the operator may include a type of the cell to be cultured. The parameter acquisition unit 304 may provide the acquired state parameter set to the calculation unit 306, the parameter input unit 310, the learning processing unit 314, the second storage unit 322, and the third storage unit 326.

[1.2.4. Calculation unit 306]

The calculation unit 306 is configured to calculate a reward value from at least one state parameter (as one example, a posterior state parameter) included in a parameter set (as one example, a posterior state parameter set.) The calculation unit 306 may provide the calculated reward value to the learning processing unit 314.

The reward value is to be determined by a predetermined reward function, and may be used for reinforcement learning of the control model 312 by the learning processing unit 314. The reward value may be a so-called KPI (Key Performance Indicator), and may indicate any one of gain obtained from the bioreactor 2, quality of the cell to be cultured, safety during the operation of the bioreactor 2 and lowness of environmental burden, for example, and may be a value obtained by comprehensive evaluation of some of the above factors. The reward value may be a value of a single state parameter itself.

Note that the calculation unit 306 may calculate a KPI from a posterior state parameter set and detect whether the target value has been reached, or may calculate a completion ratio to the target value. The calculation unit 306 may output these results to the outside of the apparatus 3. Note that to output to the outside of the apparatus 3 may be to display through a display (not shown), to print out from a printer (not shown), or to record on a recording medium.

[1.2.5. Environment Information Acquisition Unit 308]

The environment information acquisition unit 308 is configured to acquire environment information indicating an external environment of the bioreactor 2. The external environment may be at least one of an air temperature or humidity in the installation environment of the bioreactor 2. Alternatively or in addition, the external environment may include a characteristic of a raw material provided to the bioreactor 2. The environment information acquisition unit 308 may acquire the environment information from a sensor (not shown) provided at the installed location of the bioreactor 2, may acquire the environment information from the operator, or may acquire the environment information by the combination of the above. The environment information acquisition unit 308 may provide the acquired environment information to the parameter input unit 310 and the learning processing unit 314.

[1.2.6. Parameter Input Unit 310]

The parameter input unit 310 is configured to input a state parameter set (as one example, a posterior state parameter set) acquired by the parameter acquisition unit 304 to the control model 312 and the prediction unit 324. The parameter input unit 310 may additionally input environment information acquired from the environment information acquisition unit 308 to the control model 312 and the prediction unit 324.

[1.2.7. Control Model 312]

The control model 312 is a model for controlling the bioreactor 2, and is configured to output an operation content that increases a reward value in response to input of a state parameter set. When the environment information is inputted from the parameter input unit 310 in addition to the state parameter set, the control model 312 may output an operation content according to the inputted state parameter set and environment information. The operation content to output may be an operation content to be set in a state indicated by the state parameter set. The control model 312 may provide the operation content to the operation content acquisition unit 316.

The control model 312 may be subjected to a learning process by the learning processing unit 314. At an initial stage of learning, the control model 312 may output a plurality of operation contents that are different to each other in response to input of one state parameter set.

Note that, in the present embodiment, as one example, the apparatus 3 is provided with a plurality of control models 312 that are different for each type of the cell to be cultured or for each external environment. That the control models 312 are different for each external environment may be that the control models 312 are different for each condition where at least one parameter included in the environment information varies beyond a reference range.

[1.2.8. Learning Processing Unit 314]

The learning processing unit 314 is configured to execute a learning process of the control model 312 by using an inputted learning data. The learning data may include data of an operation content provided from the setting unit 302 and data of a posterior state parameter set provided from the parameter acquisition unit 304. The learning data may further include data of a prior state parameter set provided from the parameter acquisition unit 304 and may further include differential data between the prior state parameter set and the posterior state parameter set.

The learning processing unit 314 may execute a learning process by further using a reward value calculated by the calculation unit 306. In other words, the learning processing unit 314 may execute reinforcement learning.

When one operation content outputted in response to input of one state parameter set to the control model 312 is set for the bioreactor 2, and a reward value calculated from a posterior state parameter set indicating a resulting state satisfies a target condition, the learning processing unit 314 may execute a learning process of the control model 312 so that the one operation content is outputted in response to input of the one state parameter set. Thus, an operation content in which a reward value satisfies a target condition (also referred to as a suitable operation content) is uniquely determined for a state indicated by one state parameter set. The learning processing unit 314 may provide such one state parameter set and the suitable operation content uniquely determined for the state parameter set in association with each other to the output unit 320.

Note that the target condition may be that a reward value becomes higher than a reference value or becomes a maximum value. That the reward value becomes a maximum value may be that, when a plurality of operation contents are outputted from the control model 312 in response to input of one state parameter set, the reward value indicates the largest value among a plurality of reward values obtained when the plurality of operation contents are separately set.

The learning processing unit 314 may execute a learning process of distinct control models 312 for each type of the cell to be cultured. Moreover, the learning processing unit 314 may execute a learning process of distinct control models 312 for each external environment. For example, when at least one parameter included in the environment information from the environment information acquisition unit 308 varied beyond the reference range, the learning processing unit 314 may execute a learning process of distinct control models 312 before and after the variation. Note that, when distinct control models 312 are not provided for each external environment, the learning processing unit 314 may execute a learning process for a single control model 312 by including the environment information in the learning data.

In a case in which the learning processing unit 314 executes a learning process for each external environment, when a suitable operation content in which a reward value satisfies a target condition is uniquely determined for a state indicated by one state parameter set in one external environment, the learning processing unit 314 may further provide environment information indicating the one external environment in association with the one state parameter set and the one operation content to the output unit 320. The learning processing unit 314 may execute transfer learning for one external environment by using the control model 312 on which a learning process has been executed and execute a learning process for another external environment.

[1.2.9. Operation Content Acquisition Unit 316]

The operation content acquisition unit 316 is one example of a third acquisition unit, and is configured to acquire one or plurality of operation contents outputted by the control model 312 in response to input of a state parameter set to the control model 312. The operation content acquisition unit 316 may provide the acquired one or plurality of operation contents to the setting unit 302.

[1.2.10. Control Unit 318]

The control unit 318 is configured to control at least the setting unit 302, the parameter acquisition unit 304, the parameter input unit 310 and the operation content acquisition unit 316. For example, the control unit 318 may cause the bioreactor 2 to culture a cell by causing repeated serial execution of acquisition of a state parameter set by the parameter acquisition unit 304, acquisition of an operation content by the operation content acquisition unit 316, and setting of an operation content by the setting unit 302. Note that a path of a control signal outputted from the control unit 318 is omitted in FIG. 1 for simplified illustration. The control unit 318 may further control another component in the apparatus 3.

[1.2.11. Output Unit 320]

The output unit 320 is configured to output one state parameter set and a suitable operation content uniquely determined for the one state parameter set in association with each other. When one piece of environment information from the learning processing unit 314, one state parameter set, and one operation content are provided in association with each other, the output unit 320 may output these in association with each other. The output unit 320 may output the operation content to the outside of the apparatus 3.

[1.2.12. Second Storage Unit 322]

The second storage unit 322 is configured to store a learning history in a case in which a reward value satisfies a target condition. When one operation content outputted in response to one state parameter set being input to the control model 312 is set for the bioreactor 2 and then one posterior state parameter set is acquired, and a reward value calculated based on the one posterior state parameter set satisfies a target condition, the second storage unit 322 may accumulate and store the one operation content, the one state parameter set and the one posterior state parameter set in association with each other. The second storage unit 322 may store a learning history for each type of the cell to be cultured or external environment in response to input from the parameter acquisition unit 304 or the environment information acquisition unit 308, or may store a learning history independently of the type of the cell or external environment.

[1.2.13. Prediction Unit 324]

The prediction unit 324 is configured to predict a value transition according to at least one posterior state parameter when successively setting operation contents in which a reward value satisfies a target condition from a state indicated by a state parameter set acquired by the parameter acquisition unit 304.

The prediction unit 324 may execute a prediction based on a stored content of the second storage unit 322. For example, the prediction unit 324 may detect a first posterior state parameter set associated with the state parameter set acquired by the parameter acquisition unit 304 in the second storage unit 322, detect a second posterior state parameter set associated with a state parameter set having the same content as the first posterior state parameter set in the second storage unit 322, and thereafter, in a similar manner, serially detect a $n^{th}$ posterior state parameter set associated with a state parameter set having the same content as a $n-1^{th}$ posterior state parameter set (where n is an integer of 2 or greater) in the second storage unit 322. The prediction unit 324 may execute a transition prediction by identifying a value transition according to at least one posterior state parameter included in each of the first posterior state parameter set to the $n^{th}$ posterior state parameter set. When a learning history is stored for each type of the cell or external environment in the second storage unit 322, the prediction unit 324 may predict a transition based on a stored content corresponding to the relevant type of the cell or external environment among the stored contents in the second storage unit 322, according to the type of the cell or environment information inputted from the parameter input unit 310.

The value to which the transition prediction is executed may be a value of a posterior state parameter (as one example, a production amount of the cell) itself or may be the above-mentioned reward value or KPI. The prediction unit 324 may further predict another evaluation indicator according to the predicted transition and, as one example, may predict time required for culturing a target number of cells from the transition of a production amount of the cell. The prediction unit 324 may output the prediction result to the outside of the apparatus 3.

In a case in which the prediction unit 324 predicts an amount of a foreign body that exists in at least one of the bioreactor 2 or the cell, when the amount of the foreign body is predicted to exceed an upper limit value, the prediction unit 324 may inform the operator to that effect. Note that, because a foreign body is mixed in the bioreactor 2 depending on a pressure condition and grows depending on a temperature condition, the amount of the foreign body can be predicted from an operation content configured to set these conditions.

[1.2.14. Third Storage Unit 326]

The third storage unit 326 is configured to accumulate and store learning data. The third storage unit 326 may accumulate and store a set including, in association with each other, an operation content set for the bioreactor 2 and a posterior state parameter set indicating a state after the operation content is set. The third storage unit 326 may store learning data for each type of the cell to be cultured or for each external environment in response to input from the parameter input unit 310 or the environment information acquisition unit 308, or may store learning data independently of the type of the cell or external environment.

[1.2.15. Detection Unit 328]

The detection unit 328 is configured to detect a common content between operation contents corresponding to two or more particular posterior state parameter sets among a plurality of posterior state parameter sets in the third storage unit 326. The detection unit 328 may detect a common content between operation contents corresponding to two or more posterior state parameter sets that do not satisfy a reference condition. Instead or in addition, the detection unit 328 may detect a common content between operation contents corresponding to two or more posterior state parameter sets that satisfy the reference condition. When learning data is stored for each type of the cell or external environment in the third storage unit 326, the detection unit 328 may execute detection from a stored content corresponding to the relevant type of the cell or external environment among stored contents in the third storage unit 326, according to the type of the cell or environment information inputted from the parameter input unit 310 or the environment information acquisition unit 308. The detection unit 328 may execute detection independently of the type of the cell. In this case, a common content between operation contents used for learning in distinct cell cultures can be detected. The detection unit 328 may output the detection result to the outside of the apparatus 3.

That the posterior state parameter set does not satisfy the reference condition may be that any of the posterior state parameters in the posterior state parameter set or a KPI determined from any of the posterior state parameters in the posterior state parameter set does not fall within an acceptable range. As one example, that the posterior state parameter set does not satisfy the reference condition may be that the production amount of the cell does not fall within an acceptable range of from 1.1 times or more. The common content between operation contents may be that supply power to a heater is equal to or higher than a certain value, for example.

[1.2.16. Effects Obtained by the Apparatus 3]

According to the above-described apparatus 3, because learning process of the control model 312 for outputting an operation content that increases a reward value in response to input of a state parameter set is executed by using learning data including an operation content of the bioreactor 2 and a posterior state parameter set after the operation content is set, an operation content that increases a reward value can be obtained by inputting a state parameter set. Therefore, a suitable operation content can be reliably obtained without the need of trial and error by a skilled operator.

Moreover, because the bioreactor 2 is a cell culture system, a reward value according to a yield or production amount can be continuously acquired during manufacturing of the object to be manufactured. Therefore, learning can be more efficiently executed than in other manufacturing field in which a yield or a production amount is yet to be determined until completion of manufacturing.

Moreover, because the learning process of the control model 312 is executed for each external environment, a suitable operation content can be obtained even when the external environment changes.

Moreover, because transfer learning is executed by using the control model 312 on which the learning process has been executed for one external environment and execute a learning process for another external environment, learning can be completed earlier.

Moreover, because the operation content outputted in response to the state parameter set being input to the control model 312 is set for the bioreactor 2, the learning process can be repeatedly executed by operating the bioreactor 2 with the operation content according to the state parameter set.

Moreover, because a cell is cultured by repeated serial execution of acquisition of the state parameter set, acquisition of the operation content, and setting of the operation content, cell culture can be executed by using the control model 312. Therefore, when learning of the control model 312 is completed, the cell culture can be automatically executed by using a suitable operation content outputted from the control model 312. Moreover, when learning of the control model 312 is not completed, the cell culture can be executed with the operation content outputted from the control model 312 and learning process can be automatically and repeatedly executed.

Moreover, a value transition according to the posterior state parameter when successively setting operation contents in which a reward value satisfies a target condition from a state indicated by an acquired state parameter set is predicted. Thus, management of the bioreactor 2 can be facilitated.

Moreover, when an amount of a foreign body is predicted to exceed an upper limit value, it is informed to that effect, so that when the amount of the foreign body increases the culture can be stopped to improve the quality.

Moreover, because the reward value is calculated from at least one posterior state parameter included in the posterior state parameter set and a learning process is executed by using the calculated reward value, the speed of the learning process can be improved compared with that in a case in which a reward value calculated outside of the apparatus 3 is provided to the apparatus.

Moreover, a learning process is executed so that, when a reward value as a result of one operation content outputted from the control model 312 in response to input of one state parameter set being set for the bioreactor 2 satisfies a target condition, the one operation content is outputted in response to input of the one state parameter set. Thus, the learning process for a case in which the one state parameter set is inputted can be completed to prevent the learning process from being repeated wastefully.

Moreover, because the operation content corresponding to the reward value that satisfies the target condition is outputted in association with the state parameter set in a state for which the operation content is to be set, a suitable operation content under each state can be confirmed outside of the apparatus 3.

Moreover, because a common content between operation contents corresponding to two or more posterior state parameter sets that do not satisfy the reference condition among a plurality of posterior state parameter sets is detected, a content of the operation contents that causes an inappropriate state can be recognized. Moreover, because a common content between operation contents corresponding to two or more posterior state parameter sets that satisfy the reference condition among the plurality of posterior state parameter sets is detected, a content of the operation contents that causes a suitable state can be recognized.

2. Input/Output of the Control Model 312

FIG. 2 shows input/output of the control model 312 at an initial stage of learning.

In the present embodiment, as one example, the state parameter set includes values of a state parameter $I_A$ and values of a state parameter $I_B$ as a KPI. Moreover, the operation content includes values of an active variable $O_A$ and values of an active variable $O_B$. Active variables listed in one column (for example, $O_{A1}$, $O_{A2}'$, . . . ) are candidates for selectable active variables. The operation content to be output may be active variables selected in any combination from each column. As shown in FIG. 2, at the initial stage of learning, a plurality of operation contents that are different to each other are outputted in response to input of one state parameter set.

Note that state parameters $I_{A1}$, $I_{A2}$, . . . , $I_{AN}$ indicate distinct values for the state parameter $I_A$. Moreover, active variables $O_{A1}$, $O_{A1}'$, $O_{A1}''$, $O_{A2}$ indicate distinct values for the active variable $O_A$. In this context, the number of the values that the state parameters $I_A$ and $I_B$ can take is not limited to N and may be distinct from each other.

FIG. 3 shows input/output of the control model 312 after completion of learning. As shown in FIG. 3, after completion of learning, a single operation content is outputted in response to input of one state parameter set.

3. Stored Content of the Second Storage Unit 322

FIG. 4 shows a stored content of a second storage unit 322. The second storage unit 322 may store a plurality of sets including, in association with each other, a prior state parameter set, an operation content in which a reward value satisfies a target condition by being set in a state indicated by the prior state parameter set, and a posterior state parameter set after the operation content is set.
Thus, in the prediction unit 324, a prediction of a transition of the posterior state parameter set (in FIG. 4, as one example, a posterior state parameter set $(I_{A2}, I_{B2}) \rightarrow (I_{A4}, I_{B4}) \rightarrow (I_{AN}, I_{BN})$), and hence a prediction of a value transition according to any posterior state parameter is enabled.

4. Control by the Control Unit 318

Figure 5:
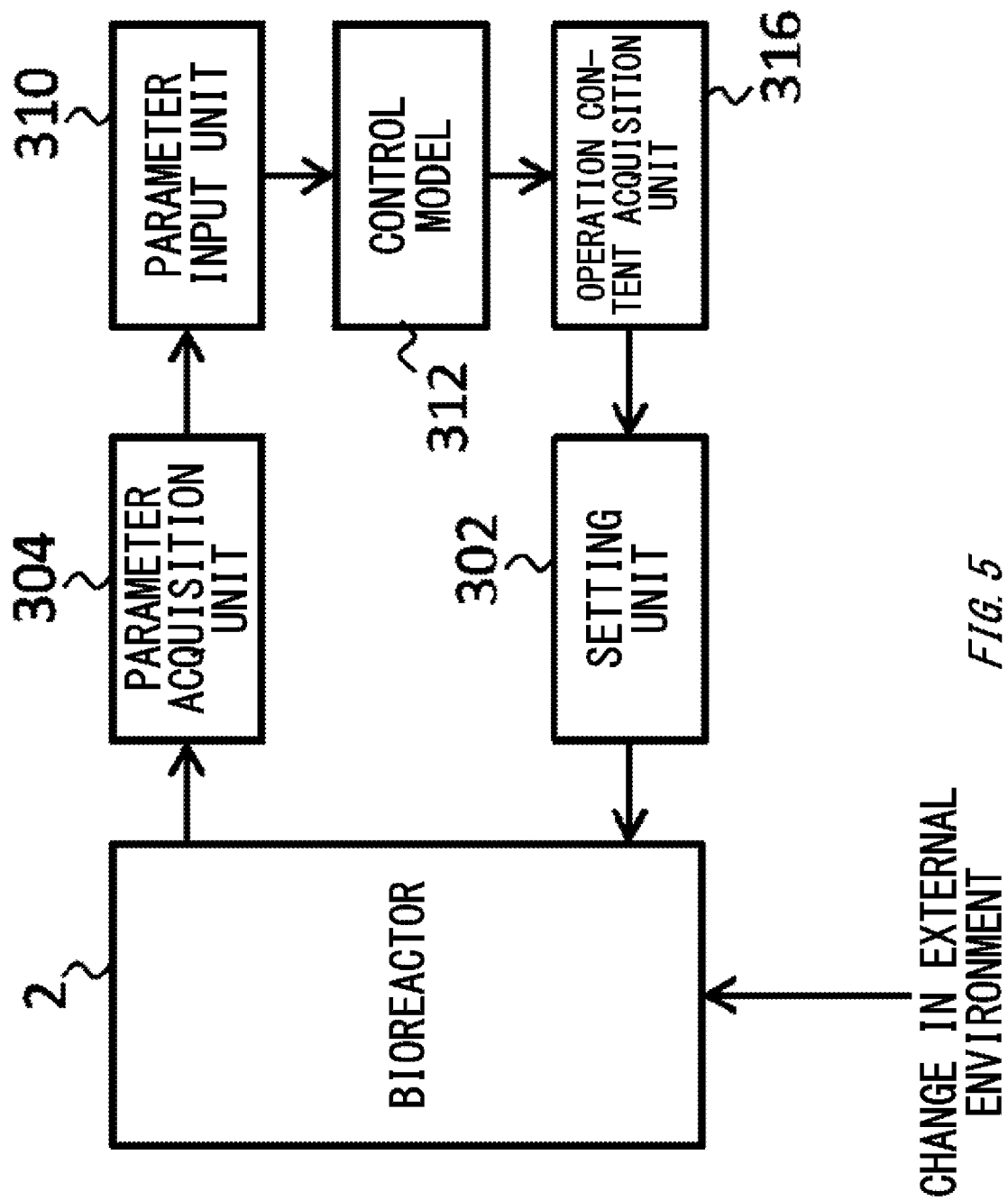
FIG. 5 shows a control content by a control unit 318.

FIG. 5 shows a control content by the control unit 318. The control unit 318 may cause the bioreactor 2 to culture a cell by causing repeated serial execution of acquisition of a state parameter set by the parameter acquisition unit 304, acquisition of an operation content by the operation content acquisition unit 316, and setting of the operation content by the setting unit 302. When a plurality of operation contents are outputted from the control model 312 in response to input of one state parameter set, the control unit 318 may cause the setting unit 302 to set each of the plurality of operation contents for the bioreactor 2 in a state indicated by the one state parameter set, and execute a search for a suitable operation content. The control unit 318 may execute a search for a suitable operation content for each external environment.

5. Operations

[5.1. Operations During Learning]

Figure 6:
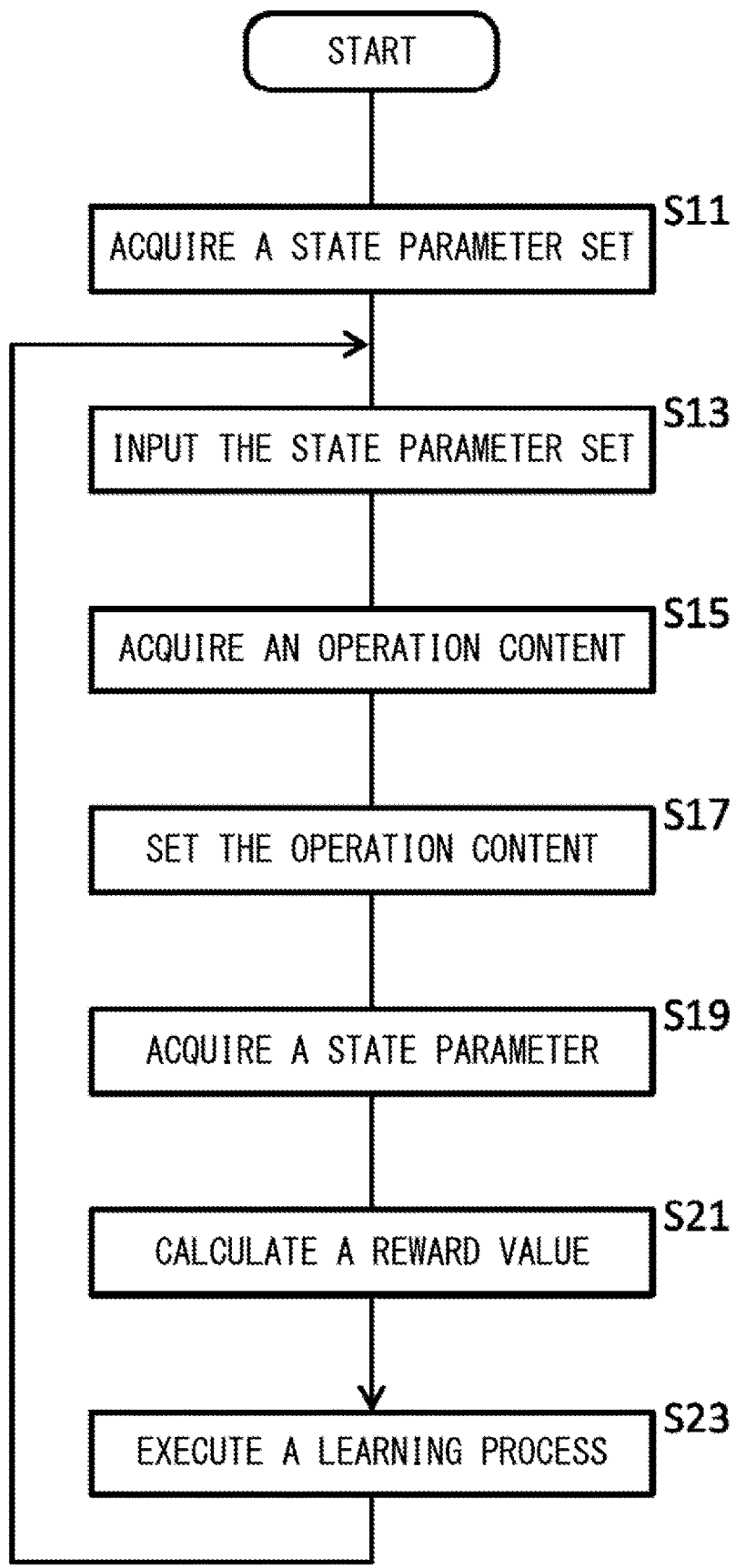
FIG. 6 shows operations of an apparatus 3.

FIG. 6 shows operations of an apparatus 3. The apparatus 3 is configured to execute learning of the control model 312 while culturing a cell in the bioreactor 2 by executing processes of Steps S11 to S23. Note that this operation may be executed for each cell to be cultured.

In Step S11, the parameter acquisition unit 304 acquires a state parameter set. The parameter acquisition unit 304 may acquire a state parameter set at the present time, for example, a prior state parameter set before setting of an operation content by the setting unit 302. Note that, in Step S11, the environment information acquisition unit 308 may further acquire environment information.

In Step S13, the parameter input unit 310 inputs the acquired state parameter set to the control model 312. When the environment information is acquired by the environment information acquisition unit 308, the parameter input unit 310 may additionally input the environment information to the control model 312 in Step S13.

Thus, an operation content that increases a reward value is outputted from the control model 312. In this context, the operation content that increases a reward value may be an operation content in which a reward value according to a posterior state parameter set after the operation content (also referred to as an posterior reward value) is set becomes higher than a reward value according to a prior state parameter set before the operation content (also referred to as a prior reward value) is set.

In Step S15, the operation content acquisition unit 316 acquires the operation content from the control model 312.

In Step S17, the setting unit 302 sets the acquired operation content for the bioreactor 2. Thus, the bioreactor 2 executes operations according to the operation content and, as a result, the cell culture proceeds, and the state of at least one of the bioreactor 2 or the cell changes.

In Step S19, the parameter acquisition unit 304 acquires a posterior state parameter set after the operation content is set in Step S17.

In Step S21, the calculation unit 306 calculates a reward value from at least one posterior state parameter included in the posterior state parameter set.

In Step S23, the learning processing unit 314 executes a learning process of the control model 312 by using learning data including data of the operation content set in Step S17 and the posterior state parameter set acquired in Step S19. The learning processing unit 314 may execute a learning process of the control model 312 according to the external environment acquired in Step S11. The learning processing unit 314 may execute a learning process by further using the reward value calculated in Step S21.

For example, when one operation content in Step S17 is set, and an increase width of a reward value calculated from a posterior state parameter set indicating a resulting state is less than a reference width, the learning processing unit 314 may execute a learning process of the control model 312 so that the one operation content is not outputted in response to renewed input of the one state parameter set inputted in Step S13 to the control model 312. The increase width of the reward value according to the result of setting of one operation content may be an increase width from a prior reward value before the one operation content is set to a posterior reward value after the one operation content is set. The reference width may be any positive values.

Moreover, when one operation content outputted in response to input of one state parameter set to the control model 312 is set for the bioreactor 2 and, as a result, the reward value satisfies the target condition, the learning processing unit 314 may complete the learning about the state indicated by the one state parameter set. Note that, in a case in which the learning processing unit 314 executes a learning process for each external environment, when one operation content outputted in response to input of one state parameter set to the control model 312 in one external environment is set for the bioreactor 2 and, as a result, the reward value satisfies the target condition, the learning processing unit 314 may complete the learning about the state indicated by the one state parameter set in the one external environment.

Note that, in the present embodiment, as one example, the control model 312 is a neural network such as a recurrent or time delay neural network, but may be another machine learning algorithm including random forest, gradient boosting, logistic regression, and support vector machine (SVM), or the like. For example, the control model 312 may include a node corresponding to each element of the learning data in an input layer and a node corresponding to each active variable of a recommended operation content in an output layer. The number of the node in the input layer corresponding to one element of the learning data may be one or plural. A intermediate layer (hidden layer) including one or plurality of nodes may be interposed between the input layer and the output layer. The learning processing unit 314 may execute a learning process by adjusting the weight of edges connecting the nodes and a bias value of an output node.

When the learning process of Step S23 is finished, the apparatus 3 shifts to the process of the above-mentioned Step S13. Thus, the processes of Steps S13 to S23 are repeated.

In this context, when learning of the control model 312 is not completed, a plurality of operation contents can be acquired in response to input of one state parameter set to the control model 312 in the processes of Steps S13 to S15. In this case, in Step S17, the setting unit 302 may set any one of the plurality of acquired operation contents so that each variation pattern in the first storage unit 300 and a variation pattern of an operation content set by the setting unit 302 do not match.

The variation patterns of the operation content set by the setting unit 302 may be variation patterns in which an operation content previously set in Step S17 and an operation content to be subsequently set in Step S17 are arranged side by side. That the variation patterns to be set and the variation patterns in the first storage unit 300 match may be that both of the variation patterns completely match or that the variation patterns at least partly match. That the set variation patterns and the variation patterns in the first storage unit 300 partly match may be that variation patterns of at least two latest operation contents among the set variation patterns and variation patterns of at least two operation contents included in series in the variation patterns in the first storage unit 300 match.

Moreover, by repeating the processes of Steps S13 to S23, an identical state indicated by one state parameter set may occur multiple times. When learning of the control model 312 is not completed, a first operation content and a second operation content in which only values of one active variable are different to each other can be outputted in response to input of the one state parameter set to the control model 312. In such case, when the difference between a posterior reward value calculated from a posterior state parameter set resulting from setting the first operation content in the state indicated by the one state parameter set and a posterior reward value calculated from a posterior state parameter set as a result of setting the second operation content in the state indicated by the one state parameter set is less than a reference width, the learning processing unit 314 may execute a learning process of the control model 312 so that an operation content that does not include the one active variable among the plurality of types of active variables is outputted in response to input of the one state parameter set in Step S23.

As one example, when one posterior state parameter set $(I_{A1}, I_{B2}, \ldots)$ is inputted to the control model 312 and a first operation content $(O_{A1}, O_{B1}, \ldots)$ and a second operation content $(O_{A2}, O_{B1}, \ldots)$ are outputted, and only the values of the active variable $O_A$ are different between the first and second operation contents and the difference between the posterior reward values is less than the reference width, a learning process may be executed so that an operation content that does not include the active variable $O_A$ is outputted in response to renewed input of the one state parameter set $(I_{A1}, I_{B2}, \ldots)$.

Then, by repeating the processes of Steps S13 to S23, one suitable operation content for the one state parameter set acquired in Step S11 is determined, and another suitable operation content for the posterior state parameter set when the one suitable operation content is set is determined. Thereafter, similarly, a suitable operation content is determined sequentially.

In this case, the output unit 320 may output the state parameter set acquired in Step S11 and a series of suitable operation contents in association with each other. In a case in which the learning processing unit 314 executes a learning process for each external environment, when a series of suitable operation contents under the same external environment are determined, the output unit 320 may output the state parameter set and external information acquired in Step S11 and the series of suitable operation contents in association with each other. The output unit 320 may further output a learning history stored in the second storage unit 322 and the control model 312 itself.

According to the above-described operations, when an increase width of a reward value according to a setting result of one operation content outputted in response to one state parameter set being input to the control model 312 is less than a reference width, a learning process of the control model 312 is executed so that the one operation content is not outputted in response to input of the one state parameter set. Thus, setting of operation contents that are unnecessary for increasing the reward value can be prevented. Therefore, the manufacturing procedure can be simplified while increasing the reward value.

Moreover, when one state parameter set is inputted to the control model 312 and a first operation content and a second operation content in which only values of one active variable are different to each other are outputted, as a result of separately setting the first and second operation contents from the state indicated by the one state parameter set, the difference between the posterior reward values may be less than a reference width. In this case, a learning process of the control model 312 is executed so that an operation content that do not include the one active variable is outputted in response to input of the one state parameter set. Thus, setting of an active variable that is unnecessary for increasing the reward value can be prevented and equipment for which the unnecessary active variable is to be set (as one example, one of a plurality of heaters) can be eliminated from the bioreactor 2. Thus, the bioreactor 2 can be simplified while increasing the reward value.

Moreover, when a plurality of operation contents are acquired in response to input of one state parameter set to the control model 312, any one operation content is set so that each variation pattern stored in the first storage unit 300 and a variation pattern of the operation content to be set do not match. Thus, by storing the variation patterns to be avoided (for example, existing variation patterns) in the first storage unit 300 in advance, new variation patterns that are different from those variation patterns can be searched.

Note that the above-described operations may be executed during a period in which the external environment does not change, and as one example, may be periodically executed during the same time in a day (as one example, during the night time from 0 o'clock to four o'clock, or the like) or may be executed during a period specified by an instruction of the operator. Moreover, the above-described operations may be executed each time the external environment changes.

Instead, the above-described operations may be continuously executed while the external environment changes. In this case, the environment information acquisition unit 308 may acquire environment information in Steps S11, S19 and the environment information acquired in Step S11 and the environment information acquired in Step S19 immediately thereafter may be different from each other. Moreover, by repeating Steps S13 to S23, the environment information acquired in Step S19 and the environment information acquired in Step S19 immediately thereafter may be different to each other. When the pieces of environment information acquired in series are different to each other, the learning processing unit 314 may execute a learning process for at least one control model 312 among distinct control models 312 according to each of the previous and subsequent pieces of environment information. Instead, the learning processing unit 314 may end the process of Step S23 without execution of the learning process when the pieces of environment information acquired in series are different to each other, and execute the learning process of the control model 312 according to the environment information only when the pieces of environment information acquired in series are the same.

[5.2. Operations During the Run]

Figure 7:
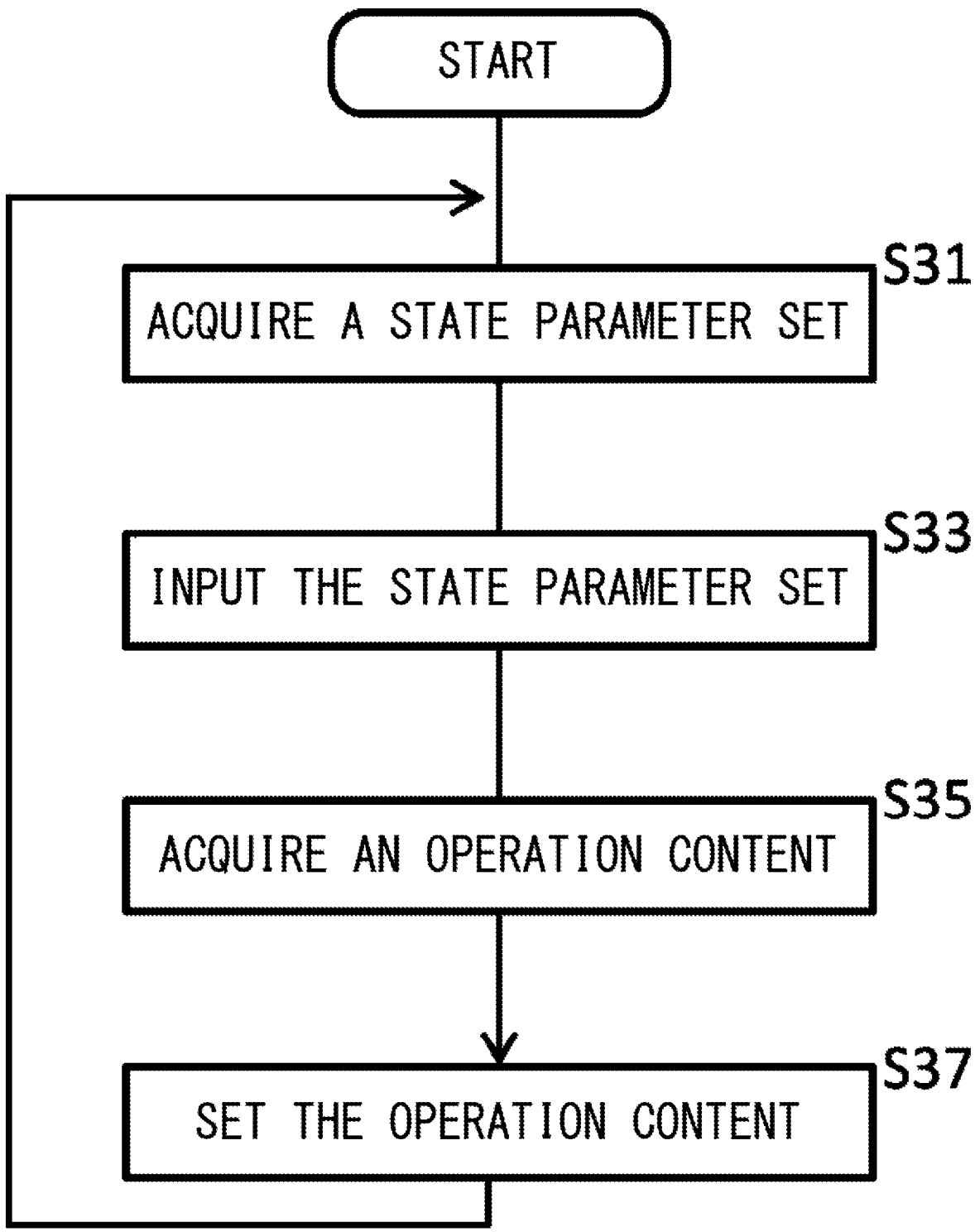
FIG. 7 shows other operations of the apparatus 3.

FIG. 7 shows other operations of the apparatus 3. The apparatus 3 is configured to culture a cell in the bioreactor 2 by using the control model 312 that completed learning by executing processes of Steps S31 to S37.

In Step S31, the parameter acquisition unit 304 acquires a state parameter set. The parameter acquisition unit 304 may acquire a state parameter set at the present time, for example, a prior state parameter set before setting of an operation content by the setting unit 302. Note that, in Step S31, the environment information acquisition unit 308 may further acquire environment information.

In Step S33, the parameter input unit 310 inputs the acquired state parameter set to the control model 312. When the environment information acquisition unit 308 acquired the environment information, the parameter input unit 310 may additionally input the environment information to the control model 312 in Step S33. Thus, one suitable operation content corresponding to the state parameter set is outputted from the control model 312.

In Step S35, the operation content acquisition unit 316 acquires the operation content from the control model 312.

In Step S37, the setting unit 302 sets the acquired operation content for the bioreactor 2. Thus, the bioreactor 2 executes operations according to the operation content and, as a result, the culture of the cell proceeds, and the state of at least one of the bioreactor 2 or the cell changes.

When the process of Step S37 is finished, the apparatus 3 shifts to the process of the above-mentioned Step S31. Thereafter, the cell culture is completed by repeated execution of the processes of Steps S31 to S37. Note that, in the present embodiment, as one example, while the operation content is set for the bioreactor 2 in Step S37, an operator may execute the setting for the bioreactor 2 by displaying it to the operator.

According to the above-described operations, an operation content that increases a reward value can be obtained by inputting a state parameter set. Therefore, a suitable operation content can be obtained without the need of trial and error by a skilled operator.

6. Variations

Note that, in the above-described embodiments, the apparatus 3 is described as including the first storage unit 300, the setting unit 302, the parameter acquisition unit 304, the calculation unit 306, the environment information acquisition unit 308, the parameter input unit 310, the one or plurality of control models 312, the learning processing unit 314, the operation content acquisition unit 316, the control unit 318, the output unit 320, the second storage unit 322, the prediction unit 324, the third storage unit 326, and the detection unit 328. However, the apparatus 3 may not include at least one of the components except the setting unit 302, the parameter acquisition unit 304 or the learning processing unit 314, or may not include the components except the parameter acquisition unit 304, the parameter input unit 310 and the operation content acquisition unit 316. Moreover, while the apparatus 3 is described as having the control model 312, the control model 312 may be provided in an apparatus external to the apparatus 3.

Moreover, while the setting unit 302 is described as configured to set any one of the plurality of operation contents acquired from the control model 312 so that each variation pattern in the first storage unit 300 and a variation pattern of the operation content set by the setting unit 302 do not match in order to avoid the variation patterns stored in the first storage unit 300, other methods may used to avoid that. For example, among a plurality of operation contents, when set by the setting unit 302, a reward value for an operation content forming a variation pattern having a match to any of the variation patterns in the first storage unit 300 may be calculated to be lower than that for an operation content forming a variation pattern having no match. Also in this case, a new variation pattern can be searched avoiding the variation patterns stored in the first storage unit 300.

Moreover, while described above as a single parameter acquisition unit 304, the first acquisition unit and the second acquisition unit may be separate components for acquiring a state parameter.

Moreover, while described above as being configured to culture a cell, the bioreactor 2 may be configured to manufacture a food, yeast or the like by a bioprocess. Moreover, while described above as a bioreactor 2, the manufacturing system may be a manufacturing plant of a beverage or metal (as one example, steel), LNG, petroleum, cosmetics, paper, pulp, or the like.

Various embodiments of the present invention may be described with reference to flowcharts and block diagrams whose blocks may represent (1) steps of processes in which operations are performed or (2) units of apparatuses responsible for performing operations. Certain steps and units may be implemented by dedicated circuitry, programmable circuitry supplied with computer-readable instructions stored on computer-readable media, and/or processors supplied with computer-readable instructions stored on computer-readable media. Dedicated circuitry may include digital and/or analog hardware circuits and may include integrated circuits (IC) and/or discrete circuits. Programmable circuitry may include reconfigurable hardware circuits comprising logical AND, OR, XOR, NAND, NOR, and other logical operations, flip-flops, registers, memory elements, etc., such as field-programmable gate arrays (FPGA), programmable logic arrays (PLA), etc.

Computer-readable media may include any tangible device that can store instructions for execution by a suitable device, such that the computer-readable medium having instructions stored therein comprises an article of manufacture including instructions which can be executed to create means for performing operations specified in the flowcharts or block diagrams. Examples of computer-readable media may include an electronic storage medium, a magnetic storage medium, an optical storage medium, an electromagnetic storage medium, a semiconductor storage medium, etc. More specific examples of computer-readable media may include a Floppy (registered trademark) disk, a diskette, a hard disk, a random access memory (RAM), a read-only memory (ROM), an erasable programmable read-only memory (EPROM or Flash memory), an electrically erasable programmable read-only memory (EEPROM), a static random access memory (SRAM), a compact disc read-only memory (CD-ROM), a digital versatile disk (DVD), a BLU-RAY® disc, a memory stick, an integrated circuit card, etc.

Computer-readable instructions may include assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, JAVA (registered trademark), C++, etc., and conventional procedural programming languages, such as the "C" programming language or similar programming languages.

Computer-readable instructions may be provided to a processor of a general purpose computer, special purpose computer, or other programmable data processing apparatus, or to programmable circuitry, locally or via a local area network (LAN), a wide area network (WAN) such as the Internet, etc., to execute the computer-readable instructions to create means for performing operations specified in the flowcharts or block diagrams. Examples of processors include computer processors, processing units, microprocessors, digital signal processors, controllers, microcontrollers, etc.

Figure 8:
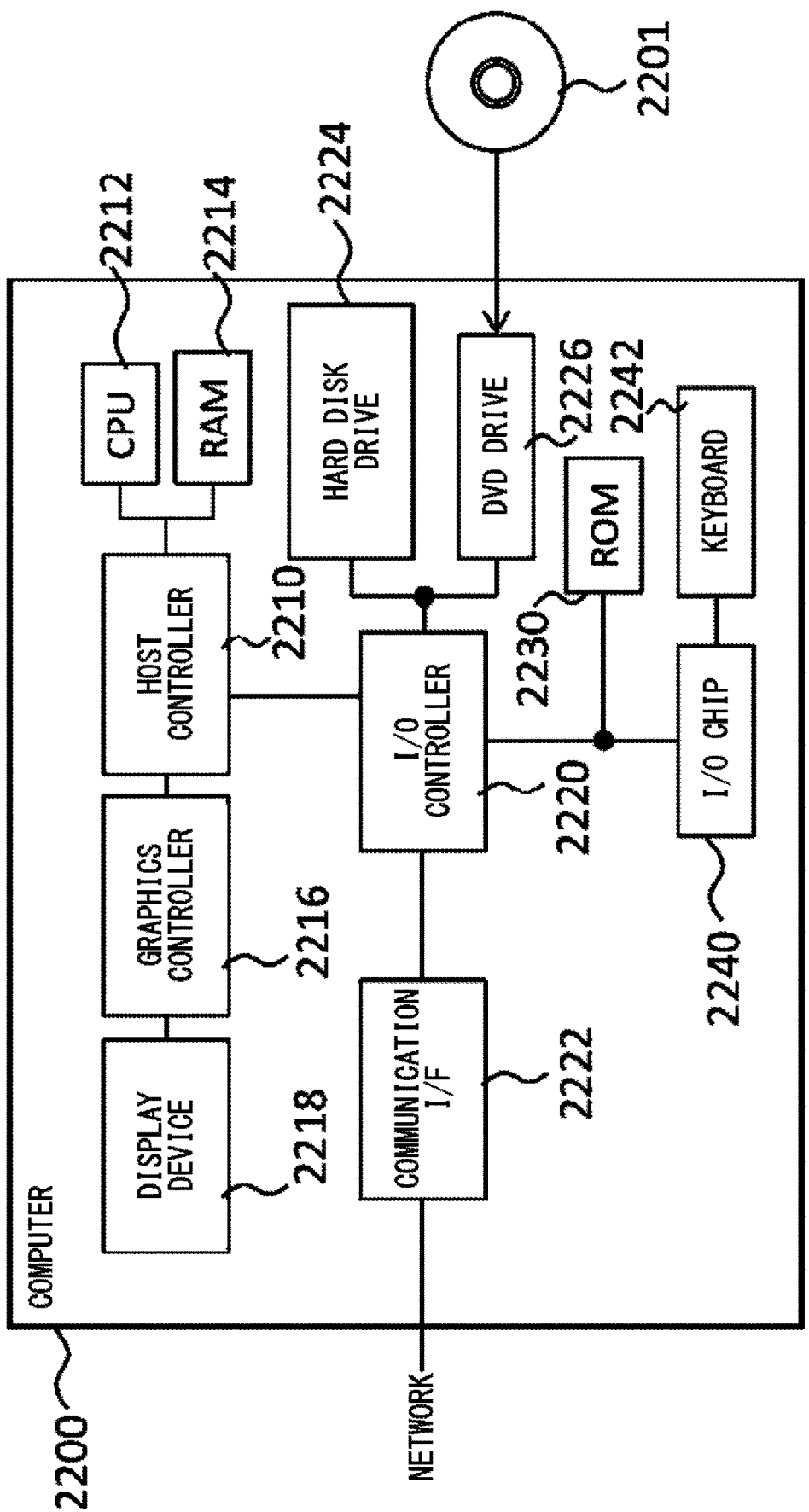
FIG. 8 shows an example of a computer 2200 in which aspects of the present invention may be wholly or partly embodied.

FIG. 8 shows an example of a computer 2200 in which aspects of the present invention may be wholly or partly embodied. A program that is installed in the computer 2200 can cause the computer 2200 to function as or perform operations associated with apparatuses of the embodiments of the present invention or one or more units thereof, and/or cause the computer 2200 to perform processes of the embodiments of the present invention or steps thereof. Such a program may be executed by a CPU 2212 to cause the computer 2200 to perform certain operations associated with some or all of the blocks of flowcharts and block diagrams described herein.

The computer 2200 according to the present embodiment includes the CPU 2212, a RAM 2214, a graphics controller 2216, and a display device 2218, which are mutually connected by a host controller 2210. The computer 2200 also includes input/output units such as a communication interface 2222, a hard disk drive 2224, a DVD-ROM drive 2226, and an IC card drive, which are connected to the host controller 2210 via an input/output controller 2220. The computer also includes legacy input/output units such as a ROM 2230 and a keyboard 2242, which are connected to the input/output controller 2220 through an input/output chip 2240.

The CPU 2212 operates according to programs stored in the ROM 2230 and the RAM 2214, thereby controlling each unit. The graphics controller 2216 obtains image data generated by the CPU 2212 on a frame buffer or the like provided in the RAM 2214 or in itself, and causes the image data to be displayed on the display device 2218.

The communication interface 2222 communicates with other electronic devices via a network. The hard disk drive 2224 stores programs and data used by the CPU 2212 within the computer 2200. The DVD-ROM drive 2226 reads the programs or the data from the DVD-ROM 2201, and provides the hard disk drive 2224 with the programs or the data via the RAM 2214. The IC card drive reads programs and data from an IC card, and/or writes programs and data into the IC card.

The ROM 2230 stores therein a boot program or the like executed by the computer 2200 at the time of activation, and/or a program depending on the hardware of the computer 2200. The input/output chip 2240 may also connect various input/output units via a parallel port, a serial port, a keyboard port, a mouse port, and the like to the input/output controller 2220.

A program is provided by computer readable media such as the DVD-ROM 2201 or the IC card. The program is read from the computer readable media, installed into the hard disk drive 2224, RAM 2214, or ROM 2230, which are also examples of computer readable media, and executed by the CPU 2212. The information processing described in these programs is read into the computer 2200, resulting in cooperation between a program and the above-mentioned various types of hardware resources. An apparatus or method may be constituted by realizing the operation or processing of information in accordance with the usage of the computer 2200.

For example, when communication is performed between the computer 2200 and an external device, the CPU 2212 may execute a communication program loaded onto the RAM 2214 to instruct communication processing to the communication interface 2222, based on the processing described in the communication program. The communication interface 2222, under control of the CPU 2212, reads transmission data stored on a transmission buffering region provided in a recording medium such as the RAM 2214, the hard disk drive 2224, the DVD-ROM 2201, or the IC card, and transmits the read transmission data to a network or writes reception data received from a network to a reception buffering region or the like provided on the recording medium.

In addition, the CPU 2212 may cause all or a necessary portion of a file or a database to be read into the RAM 2214, the file or the database having been stored in an external recording medium such as the hard disk drive 2224, the DVD-ROM drive 2226 (DVD-ROM 2201), the IC card, etc., and perform various types of processing on the data on the RAM 2214. The CPU 2212 may then write back the processed data to the external recording medium.

Various types of information, such as various types of programs, data, tables, and databases, may be stored in the recording medium to undergo information processing. The CPU 2212 may perform various types of processing on the data read from the RAM 2214, which includes various types of operations, processing of information, condition judging, conditional branch, unconditional branch, search/replace of information, etc., as described throughout this disclosure and designated by an instruction sequence of programs, and writes the result back to the RAM 2214. In addition, the CPU 2212 may search for information in a file, a database, etc., in the recording medium. For example, when a plurality of entries, each having an attribute value of a first attribute associated with an attribute value of a second attribute, are stored in the recording medium, the CPU 2212 may search for an entry matching the condition whose attribute value of the first attribute is designated, from among the plurality of entries, and read the attribute value of the second attribute stored in the entry, thereby obtaining the attribute value of the second attribute associated with the first attribute satisfying the predetermined condition.

The above-explained program or software modules may be stored in the computer readable media on the computer 2200 or near the computer 2200. In addition, a recording medium such as a hard disk or a RAM provided in a server system connected to a dedicated communication network or the Internet can be used as the computer readable media, thereby providing the program to the computer 2200 via the network.

While the present invention has been described above by way of the embodiments, the technical scope of the present invention is not limited to the range described in the above-mentioned embodiments. It is obvious to the skilled in the art that various alterations and modifications may be made to the above-mentioned embodiments. It is apparent from descriptions in the scope of claims that a mode to which such an alteration or a modification is made may also be included in the technical scope of the present invention.

It should be noted that an execution order for each processing such as the operation, the procedure, the step, and the stage in the apparatus, the system, the program, and the method illustrated in the scope of claims, the specification, and the drawings may be realized in an arbitrary order unless "ahead of", "prior to", or the like is explicitly mentioned particularly and unless the output of the previous processing is used in the subsequent processing. With regard to the operation flow in the scope of claims, the specification, and the drawings, even when the description is provided by using "first,", "next,", or the like for convenience, it does not mean that it is necessary to implement the execution in this order.

EXPLANATION OF REFERENCES

1: system, 2: bioreactor, 3: apparatus, 300: first storage unit, 302: setting unit, 304: parameter acquisition unit, 306: calculation unit, 308: environment information acquisition unit, 310: parameter input unit, 312: control model, 314: learning processing unit, 316: operation content acquisition unit, 318: control unit, 320: output unit, 322: second storage unit, 324: prediction unit, 326: third storage unit, 328: detection unit, 2200: computer, 2201: DVD-ROM, 2210: host controller, 2212: CPU, 2214: RAM, 2216: graphics controller, 2218: display device, 2220: input/output controller, 2222: communication interface, 2224: hard disk drive, 2226: DVD-ROM drive, 2230: ROM, 2240: input/output chip, 2242: keyboard

What is claimed is:

1. An apparatus comprising:
    a setting unit for setting an operation content for a manufacturing system configured to manufacture an object to be manufactured, wherein a state parameter set indicates a state of at least one of the manufacturing system or the object to be manufactured and wherein the state parameter set is referred to as a posterior state parameter set when acquired at a time point after the operation content is set by the setting unit,
    a first acquisition unit for acquiring the posterior state parameter set indicating the state of at least one of the manufacturing system or the object to be manufactured after the operation content is set, and
    a learning processing unit for executing, by using learning data including the operation content and the posterior state parameter set, a learning process of a control model of the manufacturing system configured to output the operation content that increases a reward value determined by a preset reward function in response to input of the state parameter set indicating the state of at least one of the manufacturing system or the object to be manufactured,
    wherein the learning processing unit is configured to, in a case where an increase width of the reward value according to a setting result of one said operation content outputted in response to one said state parameter set being input to the control model is less than a reference width, execute the learning process of the control model not to output the one operation content in response to input of the one state parameter set.

2. The apparatus according to claim 1, further comprising an environment information acquisition unit for acquiring environment information indicating an external environment of the manufacturing system,
    wherein the learning processing unit is configured to execute the learning process of the control model for each external environment.

3. The apparatus according to claim 2, wherein the learning processing unit is configured to execute transfer learning for one external environment by using the control model on which the learning process has been executed and execute the learning process for another external environment.

4. The apparatus according to claim 1, further comprising:
    a second acquisition unit for acquiring the state parameter set,
    a parameter input unit for inputting the state parameter set acquired by the second acquisition unit to the control model, and
    a third acquisition unit for acquiring the operation content outputted from the control model in response to input of the state parameter set to the control model,
    wherein the setting unit is configured to set the operation content acquired by the third acquisition unit for the manufacturing system.

5. The apparatus according to claim 4, further comprising a calculation unit for calculating the reward value from at least one posterior state parameter included in the posterior state parameter set,
    wherein the learning processing unit is configured to execute the learning process by further using the reward value calculated by the calculation unit.

6. The apparatus according to claim 5,
    wherein the learning processing unit is configured to, in a case where the reward value calculated by the calculation unit satisfies a target condition as a result of one said operation content outputted in response to input of one said state parameter set to the control model being set for the manufacturing system, execute the learning process of the control model so that the one operation content is outputted in response to input of the one state parameter set,
    wherein the apparatus further comprises an output unit for outputting the one operation content and the one state parameter set in association with each other.

7. The apparatus according to claim 4, further comprising a control unit for causing manufacturing of the object to be manufactured by causing repeated serial execution of acquisition of the state parameter set by the second acquisition unit, acquisition of the operation content by the third acquisition unit, and setting of the operation content by the setting unit.

8. The apparatus according to claim 5, further comprising:
    a second storage unit for accumulating and storing, in a case where one said operation content outputted in response to one said state parameter set being input to the control model is set for the manufacturing system and one said posterior state parameter set is acquired, and in a case where the reward value calculated based on the one posterior state parameter set satisfies a target condition, the one operation content, the one state parameter set, and the one posterior state parameter set in association with each other, and
    a prediction unit for predicting, based on a stored content of the second storage unit, a value transition according to at least one posterior state parameter included in each posterior state parameter set when successively setting the operation contents in which the reward value satisfies the target condition from a state indicated by the state parameter set acquired by the second acquisition unit.

9. The apparatus according to claim 8,
wherein the posterior state parameter set includes an amount of a foreign body that exists in at least one of the manufacturing system or the object to be manufactured,
wherein, in a case where the amount of the foreign body is predicted to exceed an upper limit value, the prediction unit is configured to inform to that effect.

10. The apparatus according to claim 1, further comprising:
a third storage unit for accumulating and storing the learning data, and
a detection unit for detecting, among a plurality of the posterior state parameter sets in the third storage unit, at least one of a common content between the operation contents corresponding to two or more of the posterior state parameter sets that do not satisfy a reference condition or a common content between the operation contents corresponding to two or more of the posterior state parameter sets that satisfy the reference condition.

11. The apparatus according to claim 1, wherein the manufacturing system is a system configured to culture a cell.

12. An apparatus comprising:
a setting unit for setting an operation content for a manufacturing system configured to manufacture an object to be manufactured, wherein a state parameter set indicates a state of at least one of the manufacturing system or the object to be manufactured and wherein the state parameter set is referred to as a posterior state parameter set when acquired at a time point after the operation content is set by the setting unit,
a first acquisition unit for acquiring the posterior state parameter set indicating the state of at least one of the manufacturing system or the object to be manufactured after the operation content is set, and
a learning processing unit for executing, by using learning data including the operation content and the posterior state parameter set, a learning process of a control model of the manufacturing system configured to output the operation content that increases a reward value determined by a preset reward function in response to input of the state parameter set indicating the state of at least one of the manufacturing system or the object to be manufactured,
wherein the operation content has a plurality of types of active variables actively settable for the manufacturing system,
wherein, the learning processing unit is configured to, in a case where a first operation content and a second operation content in which only values of one active variable of the plurality of types of active variables are different to each other are outputted in response to one said state parameter set being input to the control model, and the difference between reward values according to the result of separately setting each of the first operation content and the second operation content in a state indicated by the one state parameter set is less than a reference width, execute the learning process of the control model to output the operation content that does not include the one active variable of the plurality of types of active variables in response to input of the one state parameter set.

13. An apparatus comprising:
a setting unit for setting an operation content for a manufacturing system configured to manufacture an object to be manufactured, wherein a state parameter set indicates a state of at least one of the manufacturing system or the object to be manufactured and wherein the state parameter set is referred to as a posterior state parameter set when acquired at a time point after the operation content is set by the setting unit,
a first acquisition unit for acquiring the posterior state parameter set indicating the state of at least one of the manufacturing system or the object to be manufactured after the operation content is set, and
a learning processing unit for executing, by using learning data including the operation content and the posterior state parameter set, a learning process of a control model of the manufacturing system configured to output the operation content that increases a reward value determined by a preset reward function in response to input of the state parameter set indicating the state of at least one of the manufacturing system or the object to be manufactured, further comprising a first storage unit for storing a plurality of variation patterns of the operation content,
wherein, in a case where a plurality of operation contents are acquired in response to one said state parameter set being input to the control model, the setting unit is configured to set any one of the plurality of operation contents so that each variation pattern in the first storage unit and a variation pattern of the operation content set by the setting unit do not match.

14. An apparatus comprising:
a setting unit for setting an operation content for a manufacturing system configured to manufacture an object to be manufactured, wherein a state parameter set indicates a state of at least one of the manufacturing system or the object to be manufactured and wherein the state parameter set is referred to as a posterior state parameter set when acquired at a time point after the operation content is set by the setting unit,
a first acquisition unit for acquiring the posterior state parameter set indicating the state of at least one of the manufacturing system or the object to be manufactured after the operation content is set, and
a learning processing unit for executing, by using learning data including the operation content and the posterior state parameter set, a learning process of a control model of the manufacturing system configured to output the operation content that increases a reward value determined by a preset reward function in response to input of the state parameter set indicating the state of at least one of the manufacturing system or the object to be manufactured, further comprising a first storage unit for storing a plurality of variation patterns of the operation content,
wherein the reward value, in as case where it is set by the setting unit, is calculated to be lower for the operation content that forms a variation pattern that matches any of the variation patterns in the first storage unit.

15. A method comprising:
setting an operation content for a manufacturing system configured to manufacture an object to be manufactured, wherein a state parameter set indicates a state of at least one of the manufacturing system or the object to be manufactured and wherein the state parameter set is referred to as a posterior state parameter set when acquired at a time point after the setting an operation content for a manufacturing system, firstly acquiring the posterior state parameter set indicating the state of at least one of the manufacturing system or the object to be manufactured after the operation content is set, executing, by using learning data including the operation content and the posterior state parameter set, a learning process of a control model of the manufacturing system configured to output the operation content that increases a reward value determined by a preset reward function in response to input of the state parameter set indicating the state of at least one of the manufacturing system or the object to be manufactured, and executing, in a case where an increase width of the reward value according to a setting result of one said operation content outputted in response to one said state parameter set being input to the control model is less than a reference width, the learning process of the control model not to output the one operation content in response to input of the one state parameter set.

16. A storage medium having recorded thereon a program for causing a computer to function as:

a setting unit for setting an operation content for a manufacturing system configured to manufacture an object to be manufactured, wherein a state parameter set indicates a state of at least one of the manufacturing system or the object to be manufactured and wherein the state parameter set is referred to as a posterior state parameter set when acquired at a time point after the operation content is set by the setting unit, a first acquisition unit for acquiring the posterior state parameter set indicating the state of at least one of the manufacturing system or the object to be manufactured after the operation content is set, and a learning processing unit for executing, by using learning data including the operation content and the posterior state parameter set, a learning process of a control model of the manufacturing system configured to output the operation content that increases a reward value determined by a preset reward function in response to input of the state parameter set indicating the state of at least one of the manufacturing system or the object to be manufactured, wherein the learning processing unit is configured to, in a case where an increase width of the reward value according to a setting result of one said operation content outputted in response to one said state parameter set being input to the control model is less than a reference width, execute the learning process of the control model not to output the one operation content in response to input of the one state parameter set.

* * * * *